United States Patent [19]
Pontoglio et al.

[11] Patent Number: 5,206,436
[45] Date of Patent: Apr. 27, 1993

[54] TAPED PURIFICATION PROCESS

[75] Inventors: Enrico Pontoglio; Giordano Donelli, both of Brescia; Sandro Parodi, Nuvolento, all of Italy

[73] Assignee: Caffaro S.P.A., Vasto, Italy

[21] Appl. No.: 734,234

[22] Filed: Jul. 22, 1991

[30] Foreign Application Priority Data

Nov. 9, 1990 [IT] Italy .................... 22011 A/90

[51] Int. Cl.⁵ .................... C07C 233/05
[52] U.S. Cl. .................... 564/153; 564/144
[58] Field of Search .................... 564/153, 144; 252/102

[56] References Cited

U.S. PATENT DOCUMENTS 4,240,980 12/1980 Müller-Schiedmayer et al. .................... 564/153

FOREIGN PATENT DOCUMENTS 0301722 2/1989 European Pat. Off.
2832021A 1/1980 Fed. Rep. of Germany ...... 564/153
1378308 12/1974 United Kingdom ................ 564/153

*Primary Examiner*—Glennon H. Hollrah
*Assistant Examiner*—Shailendra Kumar
*Attorney, Agent, or Firm*—Henry D. Coleman; R. Neil Sudol

[57] ABSTRACT

Process for purifying, by crystallization, TAED having a titer ≧ 99.5% from a mixture containing crude TAED obtained by acetylation of DAED, wherein the purification process is performed in two different stages (1, 2), characterized in that the temperatures at which the stages are performed differ from one another (delta t) by values comprised between 55° and 110°.

8 Claims, 1 Drawing Sheet

TAPED PURIFICATION PROCESS

FIELD

The present invention relates to a process for purifying N,N,N',N', TETRAACETYLETHYLENEDIAMINE (hereinafter termed TAED for the sake of simplicity).

In particular, the present invention relates to a process for purifying TAED by crystallization which allows to obtain highly pure TAED in a microcrystalline form with the required granulometric distribution.

BACKGROUND OF THE INVENTION

TETRAACETYLETHYLENEDIAMINE (TAED) currently commercially consititutes the most important activator of the sodium perborate which is present in washing-machine detergents. It is generally produced from ethylenediamine (EDA) and acetic acid in two reaction stages: initially ethylenediamine is caused to react with acetic acid so as to form diacetylethylenediamine (DAED), through the intermediate double-salt stage; then DAED is converted into TAED by reaction with acetic anhydride by means of the intermediate stage of triacetylethylenediamine (TRIAED). Once the acetylation reaction has been exhausted, the reaction mixture is cooled, causing the crystallization of the TAED, which is isolated from the mother liquor by filtration. However, the TAED thus obtained still has, despite its high titer, traces of by-products and colored impurities and thus is not suitable for direct use in detergents, for which a perfectly colorless, odorless and controlled-granulometry product is expressly required. The TAED production cycle must therefore be completed with additional purification and granulometry-correction processes. Various proposals have been made, such as: exhaustive washings of the crystals with acetic acid and water (DE 3 609 735) or dispersion of the crude TAED in an appropriate suspension medium prior to filtration (EP 70432). However, these purification systems are not free from disadvantages, such as mainly the loss of substance and limited effectiveness.

Better results are obtained by adopting the recrystallization process which consists in hot-resolubilizing the crude TAED into acetic anhydride, in subsequently cooling the solution and then in separating the crystals from the mother liquor, which is recycled in order to avoid product losses. However, the crystals obtained with the above mentioned crystallization method are generally coarse and have wide granulometric ranges. Usually, in order to provide finer powders with well-defined and constant granulometric ranges, it is necessary to resort to additional grinding methods (EP 301 722-EP 63512).

SUMMARY OF THE INVENTION

The efforts of the Applicant have therefore been aimed at seeking a process for purifying crude TAED which is based substantially on crystallization but which can directly provide the product in the form of a microcrystalline powder which has the most appropriate granulometric distribution for formulation, without having to resort to subsequent grinding operations.

According to the invention, this result can be obtained effectively by means of a particular crystallization system which is characterized in that the temperatures of the initial solution and of the crystallization solution are kept controlled within narrow ranges and the crystallization temperature is reached by means of a virtually instantaneous cooling.

The practically instant reaching of high supersaturation values determines a high production of crystalline nuclei and thus a greater fineness and a narrower granulometric distribution of the product.

The aim of the present invention is therefore a process for purifying, by crystallization, TAED having a titer $\geq 99.5\%$ from a mixture containing crude TAED obtained by acetylation of DAED, wherein said purification process is carried out in two different stages, characterized in that the temperatures at which said stages are carried out differ from one another (delta t) by values comprised between 55° and 110° C., and preferably between 70° and 80° C.

A further object of the present invention is the purified TAED according to the above process.

BRIEF DESCRIPTION OF THE DRAWING

In practice, the process according to the present invention can conveniently but non-limitatively be performed by using the apparatus the diagram whereof is illustrated in the accompanying figure. Said apparatus essentially consists of two sections: a feed section and a crystallization section.

DETAILED DESCRIPTION

Figure 1:
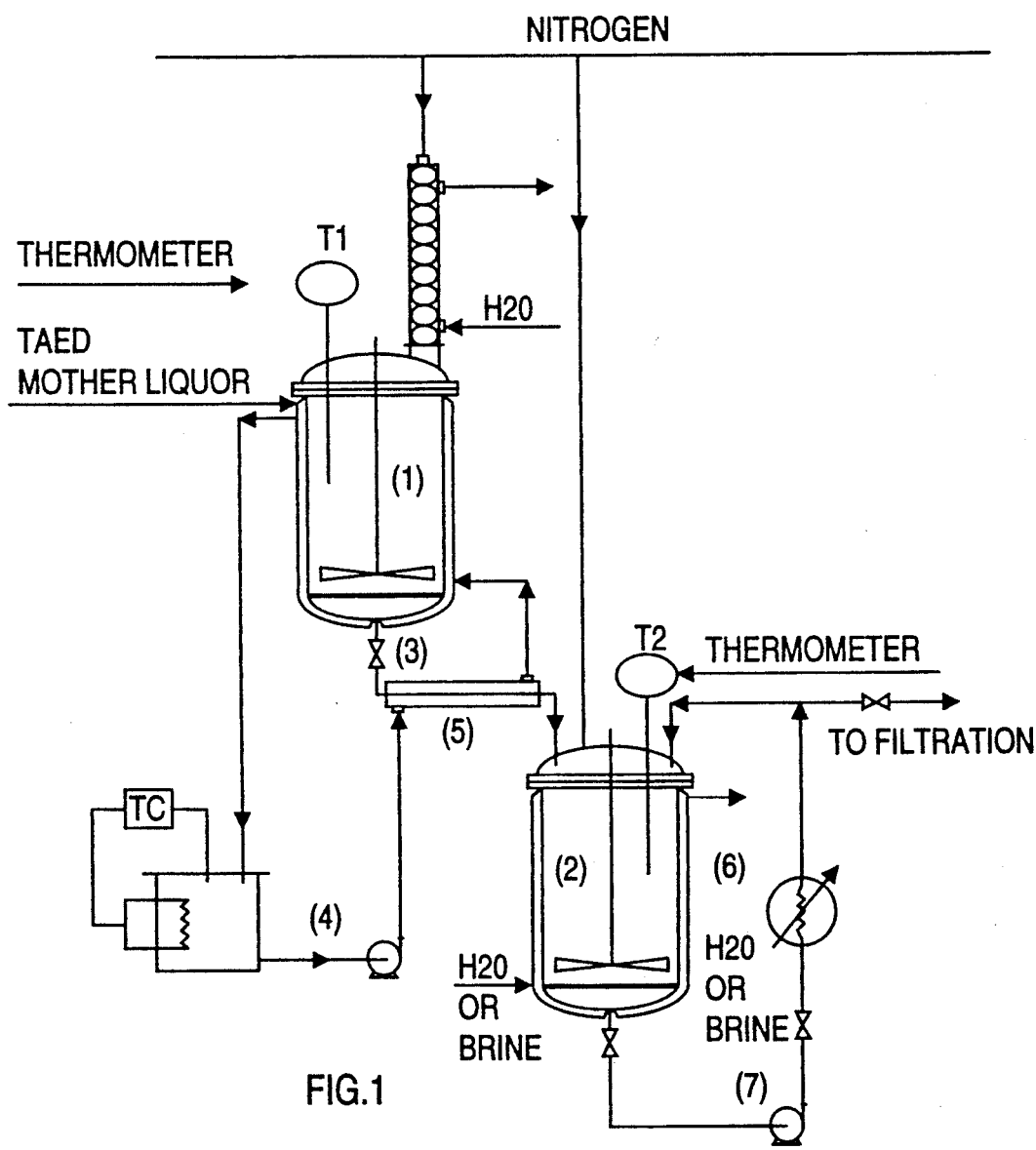

In the first section, represented by an agitated reactor 1 which is appropriately heated by circulating a thermostatic liquid 4 in the jacket, the acetic solution of impure TAED is prepared by heating to between 80° and 120° C., preferably between 100° and 110° ($T_1$), the crude substance in pure acetic anhydride or preferably in a mixture with the recycled mother liquor arriving from the filtration step. The concentrations are kept very close to the saturation values referred to the temperature being used, for example approximately 36% at 105° C. This solution is then sent, by means of the heated line 5 and of the feed valve 3, into a second reactor 2 (crystallization section) which is loaded with acetic anhydride or, better still, with a homologous crystalline suspension which is constantly kept at a temperature comprised between $+30°$ C. and $+65°$ C. and kept agitated both by the mechanical agitator and by an external recirculation system obtained by aspirating, by means of the pump 7, the suspension from the bottom of the reactor.

The crystallization unit is cooled by circulating water or brine both in the reactor's jacket and in a heat exchanger 5 inserted on the recirculation line of the suspension, so as to maintain a difference in temperature, between the feed solution and the crystalline suspension (delta $T = T_1 - T_2$), comprised between 55° and 110° C., preferably 70° and 80° C., this difference (delta t) being critical according to the invention.

The suspension is then continuously discharged and sent to filtration (not illustrated in the drawing), separating the crystals from the mother liquor, which is recycled to the feed section.

Therefore, according to the invention, the process can be performed continuously or discontinuously, depending on whether the solubilization of the crude TAED is performed intermittently or not.

In any case, a purification cycle is obtained which is faster than conventional crystallization methods and is thus more advantageous from the productive point of view. After drying, the crystals are colorless and odorless, with a TAED titer of more than 99.5, and at the same time the granulometric distributions are rather narrow and the average diameter of the particles, without having to resort to any type of grinding, can be varied by acting on the difference between the temperature of the solution and the crystallization temperature, always obtaining particularly uniform granulometric distributions. In particular, it is easy to obtain microcrystalline powders having particle sizes comprised between 40 and 250 μ with 80% by weight comprised between 40 and 100 μ without performing any grinding.

To conclude, therefore, by means of the process which is the subject of the present invention the characteristics of the product thus obtained are such as to make it suitable for use in the formulations of detergents, bleaching products or disinfectants, adding it directly in powder or in granules after an adequate agglomeration process.

The following examples are illustrative but non-limitative.

The parts (p) are to be considered as parts by weight unless otherwise specified.

EXAMPLE 1

An apparatus was used which follows the layout of the accompanying drawing and is substantially constituted by two glass reactors, each having a capacity of five parts/volume, cascade-connected so that the feed occurred by gravity and remained fixed by adjusting the opening of the valve of the bottom discharge of the first reactor 3.

The test was performed discontinuously but consecutively in order to simulate steady-state conditions in the crystallization unit.

The procedure was the following:

Approximately 1.6 p of crude TAED and 3 p of mother liquor were loaded intermittently into the first reactor until a clear solution at 104°-106° C. was obtained. Simultaneously, the agitation and the external recirculation of the crystalline suspension, present in the second reactor and deriving from a preceding test, was started. Feeding of the solution then began at a rate of approximately 11 p/h, maintaining a temperature between +25° C. and +35° C. in the crystallization unit by cooling.

The pulp, which was drawn continuously, was sent to filtration. The crystals, after washing with water, were dried in a fluidized bed with hot air at 70° C. and finally classified by wet screening.

The granulometric distribution was, on the average, as follows:

| 0–40 | μ | 4.8% |
|---|---|---|
| 40–100 | μ | 82% |
| 100–250 | μ | 13% |
| >250 | μ | 0.2% |

EXAMPLE 2

Using the same apparatus and operating in a manner identical to that described in example 1, the crystallization tests were repeated, except for the temperature in the crystallization unit, which was kept between 0° and +10° C.

After the usual filtration, washing and drying operations, the average granulometric distribution was:

| 0–40 | μ | 21% |
|---|---|---|
| 40–100 | μ | 77% |
| 100–250 | μ | 2% |
| >250 | μ | — | thus with a shift of the crystal population toward the smaller sizes as the value of delta T ($T_1-T_2$) rises.

EXAMPLE 3 (COMPARISON EXAMPLE)

For comparison with the preceding examples, the dimensional analysis of a sample of TAED purified with the conventional recrystallization method, i.e. obtained by 36% solubilization of crude TAED in acetic anhydride at 106° C. and by subsequent gradual reduction of the solution's temperature, so as to reach ambient values in approximately 2 hours, is indicated.

| 0–40 | μ | 0.5% |
|---|---|---|
| 40–100 | μ | 3.5% |
| 100–250 | μ | 18% |
| >250 | μ | 78% |

We claim:

1. A process for the production of microcrystalline TAED from a solution containing acetic anhydride and crude TAED obtained by acetylation of DAED, said microcrystalline TAED having a titer of at least 99.5% and particle sizes in the range of from 40 to 250 microns with about 80% by weight in the range of from 40 to 100 microns, said process being performed in two steps at different temperatures, a first of said steps (a) comprising heating a solution containing a concentration of TAED very close to saturation at a temperature between 80° and 120° C. and a second of said steps (b) comprising crystallizing TAED by instantaneously cooling said heated solution at a temperature 55 to 110 degrees below the temperature of said solution of step (a), said microcrystalline TAED being obtained without the use of a grinding step.

2. The process according to claim 1 wherein said heated solution is instantaneously cooled at a temperature 70° to 80° C. below the temperature of said heated mixture.

3. The process according to claim 1 wherein said first stage comprises heating said solution at a temperature between 100° C. and 110° C.

4. The process according to claim 1 wherein said first stage comprises heating said solution at a temperature between 104° and 106° C. and said second stage comprises crystallizing TAED by instaneously cooling said heated solution at a temperature of 25° C. to 35° C.

5. The process according to claim 1 wherein said first stage comprises heating said solution at a temperature between 104° and 106° C. and said second stage comprises crystallizing TAED by instaneously cooling said heated solution at a temperature of 0° C. to 10° C.

6. The process excluding the use of any grinding step for the production of microcrystalline TAED having a titer of at least 99.5% and most particle sizes in the range of from 40 to 100 microns from a solution containing acetic anhydride and crude TAED obtained by acetylation of DAED comprising:

(a) heating a solution of TAED having a concentration close to saturation at a temperature of 80° C. to 120° C. in a first unit;

(b) feeding the heated solution of said step (a) into a second unit containing a crystalline suspension of TAED kept at a temperature 55° to 110° C. below the heated solution to instantaneously cool said heated solution from step (a) and produce microcrystalline TAED.

7. The process according to claim 6 wherein said cooled crystalline suspension of TAED is kept at a temperature 70° to 80° C. below the heated solution.

8. The process according to claim 6 wherein said TAED solution in said first step is heated at a temperature between 100° C. and 110° C.

* * * * *